Figure 1:
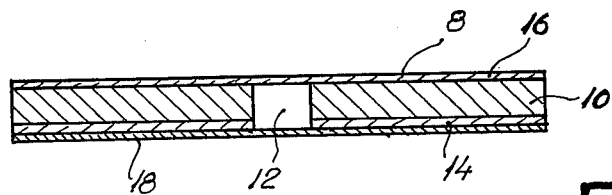

United States Patent [19]

Poulsen et al.

[11] Patent Number: 4,460,392
[45] Date of Patent: Jul. 17, 1984

[54] FILTER FOR OSTOMY BAGS

[75] Inventors: Finn Poulsen, Vaerløse; Peter Samuelsen, Rungsted Kyst; Niels O. Johannesson, Espergaerde; all of Denmark

[73] Assignee: Coloplast A/S, Espergaerde, Denmark

[21] Appl. No.: 469,479

[22] Filed: Feb. 24, 1983

[30] Foreign Application Priority Data

Feb. 23, 1982 [DK] Denmark .................................. 776/82

[51] Int. Cl.³ .............................................. B01D 50/00
[52] U.S. Cl. ..................................... 55/385 C; 55/387; 55/514; 55/359; 55/524; 604/333
[58] Field of Search ................... 55/278, 514, 385 C, 55/387, 359, 524; 604/333

[56] References Cited

U.S. PATENT DOCUMENTS

| | | | |
|---|---|---|---|
| 4,203,445 | 5/1980 | Jessup | 604/333 |
| 4,234,326 | 11/1980 | Bailey et al. | 55/387 |
| 4,274,848 | 6/1981 | Gro | 55/387 |
| 4,318,406 | 3/1982 | McLeod | 604/333 |
| 4,340,402 | 7/1982 | Catron | 55/514 |
| 4,373,635 | 2/1983 | Mules | 55/359 |

Primary Examiner—Bernard Nozick
Attorney, Agent, or Firm—Lawrence Rosen

[57] ABSTRACT

In a deodorizing gas filter for ostomy bags (22), consisting of a sheet (10) of deodorizing filter material, for example a porous foamed plastic with particles of active carbon, and having a central inlet opening (12), a gas-tight connecting layer (14) to the bag on one side of the filter sheet, and a gas-tight covering layer (24) on the other side of the filter sheet, the covering layer consists of elastic film material, or is provided with a layer of elastic material at least in that part covering the central opening and an immediately surrounding zone thereof.

This makes it possible to prick through the covering layer (24) and via the central opening also the bag in one with a needle, and still secure the desired passage of gas from the central opening (12) centrifugally through the filter, since the elastic material of or on the covering layer results in the needle hole closing and remaining closed at the pressures practically occurring in ostomy bags, whereas the needle hole in the bag, having the form of one or more short tears, remains open because the bag film is of a thermoplastic inelastic material.

Possibly, the filter (28) affixed to the bag (22) may be covered with a cover (34) to prevent carbon particles possibly falling out from the filter sheet (10) from dirtying the ostomy bag, said cover being tearable on account of a weakening line (38).

7 Claims, 3 Drawing Figures

FILTER FOR OSTOMY BAGS

TECHNICAL RANGE

The present invention relates to an odour-removing filter for ostomy bags and similar aids.

TECHNICAL BACKGROUND

Bags for collecting fecal material and other excretes from colostomies, ileostomies and other artificial and natural openings of the body are often supplied with or designed for affixing a filter in order to avoid the bag from being blown up by internal gases, and so as to vent the gases without creating bad smells.

The Danish patent specification No. 141,392 discloses such a venting member containing an odour removing filter material enclosed between walls which are impervious to gases and liquids, and where the filter material itself, which is normally in the form of a disc, is adhesively connected to the walls that are impervious to gases and liquids. Other forms of such filters are also known, e.g. from the Danish patent specifications No. 130,277, No. 133,080 and No. 135,303.

A filter consisting of a flat filter disc made from odour removing material and having a central opening is in the market; on one side the filter disc is provided with a self-gluing adhesive, possibly in the form of a film which is glued or welded to the filter disc and carries a self-gluing adhesive on the face opposite to the filter disc. Generally, this filter is supplied separately (but can also be affixed to an ostomy bag by the manufacturer); in use it is affixed to the ostomy bag at a suitable place and the ostomy bag is perforated with a needle within the range defined by the central opening in the filter disc. A cover disc of gastight material is then glued to the free side of the filter disc so as to hermetically seal the whole filter disc and its central opening. Gas from the ostomy bag can pass through the perforation of the bag, but is stopped by the covering disc. Therefore, it must pass through the filter disc and after deodorizing here, it vents to the surroundings through the rim of the disc which is not covered by the covering disc.

Even if this known filter has proved appropriate in many respects, it has in certain circumstances certain disadvantages. It may e.g. be undesireable that the filter device is in several separate parts. Particularly when it is wanted to supply the bag with affixed filter, it is more practical that it is quite finished so that several different parts do not have to be joined together to form the finished bag.

Hitherto, filters have not been used at ileostomy because the fecals are here liquid and could easily block the perforation in the wall of the bag. If this takes place, a new perforation might be necessary.

At ileostomy and at colostomy and in cases of a big amount of intestine gas it may be that a perforation made by the manufacturer in the bag inside the filter, or a perforation pricked by the user, is too small to vent the intestine gas quickly enough to avoid blowing up of the bag and in that case it is desireable that one or more openings can easily be provided by the patient.

When one or more holes have to be pricked, no matter what is the reason, the covering disc must first be removed, since the gases can escape directly without passing the filter if the covering disc is also pricked through. The self-gluing adhesive is not always suited for reuse, wherefore it may be necessary to apply a new covering disc, which the user is then forced to have present, and if the adhesive is particularly strongly gluing, and the covering disc is exactly fitting the filter and precisely placed, it may be difficult to remove it.

THE INVENTION

It is the object of the invention to solve the said problems. Thus, the invention relates to an odour removing gas filter for application to or applied to an ostomy bag or similar aid and consisting of (a) a sheet of gas penetrable, porous, odour removing filter material with a central inlet for the gases to be deodorized, which after passage through the filter in a centrifugal direction leave it at its outer rim, (b) a gas-impervious layer connected to one side of the filter sheet and either consisting of or leaving on the side opposite to the sheet, a self-gluing adhesive, or consist of a film which is welded or can be welded to the bag, the said connected layer being in total surface contact with the sheet and having a central opening of substantially the same size and form as, and being aligned with the central opening of the filter sheet, (c) a gastight covering layer on the other side of the sheet being in full surface contact with the sheet by means of gluing, welding or in other manner, and further covering the central opening of the sheet, and (d) possibly a removable protecting cover. The gas filter of the invention is characterized in that the covering layer consists of an elastic film material or has, at least in that part covering the central opening and an immediately surrounding zone thereof, a layer of elastic material.

It has been found that when the covering layer or at least the part thereof which is placed above the central opening of the filter and in a narrow zone immediately surrounding the central opening is of elastic material, one is able, if the original opening in the bag is clogged or is too small, to prick a new hole by passing a needle or similar tool through the covering layer and the bag film material without risk of the gases venting directly through an opening in the covering layer without being deodorized, instead of passing through the filter material. This is due to the hole in the elastic material closing and remaining closed at the pressures normally occuring in ostomy bags, if only the elastic film is sufficiently thick.

If an inelastic film of for instance polyethylene, polyvinyl chloride, polyester or nylon is perforated with a needle, the opening will typically appear as one or more tears radiating from the entry of the point of the needle. The longest tear will typically be longer than the diameter of the needle, and be at least as long as said diameter. On account of remaining deformation of the film, the needle will generally leave a visible hole. Inelastic films will therefore be leaky even at small differences of pressure.

If a hole is pricked in an elastic film, for example of natural rubber, polyurethane gum, isoprene gum, ethylene-propylene gums, silicone gum, butadiene gum or butyl gum, the hole will also typically appear as tears but due to elastic deformation of the material, the tears will be quite short. Further, since the film does not assume a lasting deformation on account of its elasticity, the perforation will not leave a visible hole. At great differences of pressure, gases will open the hole and pass through, but at the pressures normally occuring in ostomy bags, the gases will not be able to open the hole in reasonably thick films.

If the hole made by the manufacturer or first being pricked in the film by the user should be stopped during use of the ostomy bag, or if its capacity for passage of gas is too small, a new hole can simply be pricked without altering the properties of the filter, because the hole in the elastic cover layer will close as explained above, and the gas will thus be forced to pass through the filter.

SHORT DESCRIPTION OF THE DRAWING

The drawing shows in cross section:
FIG. 1 an embodiment of the filter of the invention,
FIG. 2 another embodiment in which the filter is affixed to an ostomy bag, and
FIG. 3 a third embodiment in which also the filter is affixed to an ostomy bag.

It should be noted that all three figures show the filter in excessive size, and that the size relationship between the individual parts, particularly between the thickness of the individual layers, is not necessarily correct.

EMBODIMENTS OF THE INVENTION

The filter 8 shown in FIG. 1 consists of the proper filter 10 having on its underside a connecting layer 14 and on the upperside a covering layer 16, both pasted onto the filter 10.

The filter 10 itself is of known type. It can consist, for instance, of matted films, such as filter paper, or of an open-celled foamed plastic, such as foamed polyurethane, in both cases containing powder particles of active carbon, which is the deodorizing material in the filter. Also other deodorizing materials could be used, for example amines or strongly oxidizing components such as chlorine dioxide. The filter 8 can have an arbitrary shape, for example as a circular disc or a polygonal sheet with more or less rounded corners. Appropriately, the filter is circular with a diameter of about 3 cm or square with rounded corners and a side length of about 3 cm. Centrally, the proper filter disc 10 has a preferably circular opening, for example of 4 mm diameter. The opening can be excentrically placed, but the shortest passage way from the opening to the nearest border of the filter should be reasonably long, for instance at least 1 cm, in order to ensure good deodorization of the gases passing through. The filter disc 10 can for instance be of 2 mm thickness.

The connecting layer 14 must be gas tight and in full surface contact with the filter disc 10. In the present specification this means that there is solid connection between all of the respective adjoining surfaces, allowing for no interspaces through which gases could pass between the surfaces and thus flow outside the filter itself. It is of no importance whether the surface contact is established by pasting, welding or otherwise as long as no interspaces or channels occur. Thus, spot welding or line pasting would not be sufficient. In the present specification pasting is to be understood as joining together, possibly under influence of heat, of two identical or different materials by means of a material different from one or both, or of two different materials by means of one of the materials if it is thermoplastic. By welding is to be understood the uniting of two identical materials by thermoplastic flouring.

The connecting layer 14 of the shown embodiment consists of a thin inelastic film provided on both sides with an adhesive. Thus, its surface is solidly connected to the filter disc 10. The adhesive on the film 14 is self-sticky, pressure-sensitive, whereby the filter 8 can easily be mounted upon a not shown ostomy bag. Opposite the opening 12 in the filter disc 10, the connecting layer 14 has a corresponding opening of the same size and outline.

The connecting layer does not necessarily need to be an individual film disc, but may simply consist of a gas-tight layer of a self-sticky, pressure-sensitive adhesive which totally closes the pores in the bottom surface of the filter disc 10.

On the upper side of the filter disc 10 and in full surface contact with it, a gas-tight covering layer 16 is provided, also covering the opening 12. The covering layer 16 consists of an elastic film, e.g. of one of the hereinbefore named materials, particularly appropriate of polyurethane which has also thermoplastic properties.

On the bottom side of the connecting layer 14 is a removable protecting cover 18, for instance consisting of paper covered with silicone. The protecting cover can be a band or a larger sheet of paper carrying a number of filters 8 affixed by means of the self-sticky adhesive layer on the bottom side of the connecting layer 14.

When the filter 8 is to be used, it is removed from the protecting cover 18 and glued to the ostomy bag. All known ostomy bags are manufactured from inelastic film material. A hole is pricked with a needle through the covering layer 16 opposite the opening 12 so that the needle is passed through the latter and also pricks a hole in the bag opposite the opening 12.

Of the hereinbefore explained reasons, the hole in the bag film will be permanent and allow gases to pass, whereas the hole in the elastic covering layer will close and block the direct passage of the gases to the surroundings. In known manner, therefore, the gases are forced to enter the filter disc 10 through its border against the opening 12, pass through the filter disc and leave it through its outer periphery in deodorized state.

The necessary or desirable thickness of the elastic covering film 16 is dependant on the nature of the material, but generally it has been found that in strongly elastic materials the thickness can be as small as $30\mu$. If the film is of polyurethane, the covering layer 16 has appropriately a thickness of 50–400, particularly expedient of about $150\mu$, according to the invention.

The connecting layer 14 can consist of a suitable plastic film material and be thin.

Figure 2:
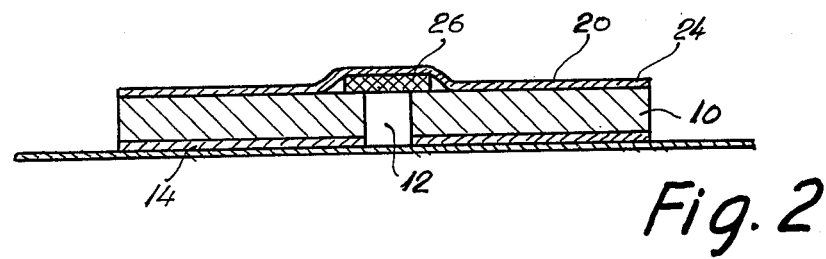

The filter 20 shown in FIG. 2 like the filter 8 has a filter disc 10 with a connecting layer 14, both having the central opening 12. Here the filter is pasted to one wall 22 of an ostomy bag and has not, therefore, the removable protecting cover 18. On the upper side, the filter disc 10 fully contacts a covering layer 24 consisting of an inelastic film; the thickness of the latter is not particularly important if only it is sufficient to ensure total gas tightness against oozing of gases directly from the upper side of the filter disc.

To ensure that the object of the invention is attained, a small sheet or lump 26 of elastic material, principally of the same kind as the covering layer 16 in the filter 8, is placed over the opening 12 and a narrow adjoining zone around the latter between the filter disc 10 and the covering film 24, said sheet or lump 26 being fastened to both the filter disc 10 and the covering layer 24.

As regards the thickness of the sheet 26, the same as hereinbefore said applies the thickness of the covering layer 16. The sheet 26 should extend over a zone of suitable width of the filter disc 10 around the opening 12; the said zone shall ensure the possibility of a suitable joining to the filter disc 10 and also ensure that the tears made by entering of the needle do not extend to the rim of the sheet 26 to possibly communicate with tears in the covering film 24. Appropriately, the radial width of the zone is at least 1 mm, and preferably 2-3 mm. The borders of the sheet 26 opposite to the filter disc 10 could possibly be levelled to ensure that no interspaces are created between the filter disc 10 and the covering film 24.

Figure 3:
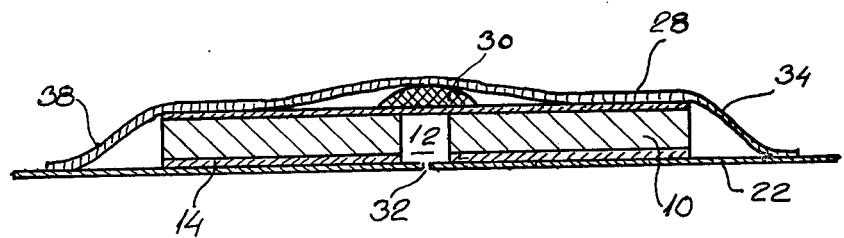

A production-technically simpler use of the principle illustrated in FIG. 2 appears from FIG. 3. A filter 28 with a filter disc 10, a connecting film 24 and a central opening 12 is pasted to a wall 22 of an ostomy bag; in the case, the manufacturer has provided the ostomy bag with a small hole opposite the opening 12. On the upper side of the filter disc 10, an inelastic covering film 24 has been pasted with total surface contact. On the side of the film 24 opposite to the filter disc 10 is a lump of elastic material 30. The material could be a film material as in FIG. 2, but in the shown embodiment it is a lump of silicone gum, affixed in the manufacture as a drop of viscous silicone gum which is self-curing or contains an evaporating solvent. The thickness of the lump is not particularly critical. It should be at least 50µ and may be up to for instance 1.5 mm.

It has been found that sometimes during transport of the filters, the carbon particles may tend to fall out from the filter sheet 10. Since they are very visible according to their nature, this may result in a conspicuous even if limited and innocuous dirtying of the bag with attached filter within the package. To avoid this, the filter 28 is so to say encapsulated in a protecting cover 34, which in the shown embodiment is of the same kind of film as the wall 22 of the bag. The cover 34 is slightly bigger than the filter 28 thus extending a little from this on all sides. By an annular welding line 36, it is thightly welded to the film 22 of the bag, but could also be pasted thereto. In order to be easily removed when the bag is to be used, the protecting cover 34 is provided with a weakening line 38, for example in the form of reduced thickness of the material. Here, the weakening line is annular, but could also, for instance, be formed as a cross over the protecting layer 24.

Appropriately, the covering layer is also provided with a strap or flap (not shown) for use to grip with the fingers to tear the layer.

We claim:
1. A deodorizing gas filter applied to or for being applied to an ostomy bag or similar aid, consisting of
(a) a sheet (10) of gas penetrable, porous, deodorizing filter material with a central inlet (12) for the gases to be deodorized, which after passage through the filter in a centrifugal direction leave it at its outer rim,
(b) a gas-impervious connecting layer (14) on one side of the sheet (10), either consisting of or having a self-gluing adhesive on the side opposite to the sheet, or consisting of a film which is welded or can be welded to the bag, the said connecting layer being in total surface contact with the sheet (10), and having a central opening of substantially the same size and form as, and being aligned with the central opening (12) of the filter sheet,
(c) a gas-tight covering layer (16,24) on the other side of the sheet (10) being in full surface contact with the sheet (19) by means of gluing, welding and covering its central opening (12), and
(d) a removable protecting cover, characterized in that the covering layer (16) consists of an elastic film material or when non elastic has, at least in that part covering the central opening and an immediately surrounding zone thereof, a layer of elastic material.

2. Gas filter according to claim 1, characterized in that the protecting cover (24) consists of inelastic material, and that a sheet or lump (26) of elastic material is placed between the covering layer (24) and the filter sheet (10) over the opening (12) and a zone around the latter.

3. Gas filter according to claim 1, characterized in that the covering layer (24) consists of inelastic material, and that it has, on the side opposite to the filter sheet (10), a sheet or lump (30) of elastic material outside the central opening (12) and a zone around the latter.

4. Gas filter according to claim 1, characterized in that the protecting cover (16) wholly consists of polyurethane film and has a thickness of at least 30µ.

5. Gas filter according to claim 1 or 4, characterized in that the protecting cover (16) consists of polyurethane film and has a thickness of 50-400µ, preferably about 150µ.

6. Filter according to any of claims 1 to 3, characterized in that the removable protecting cover (18) is on the side of the connecting layer (14) which is opposite to the filter sheet (10) and in known manner consists of with wax or silicone covered paper and that a number of filters are removably fastened to a sheet of such material.

7. Filter according to any of the preceeding claims 1 to 3, characterized in that the filter is mounted on an ostomy bag (22) by welding or pasting, and that the protecting cover (34) consists of thermoplastic film, preferably of the same kind as the bag (22), the film being bigger than the filter (28) and, in a zone (36) totally surrounding the filter, being pasted or welded to the bag, whereas the protecting cover has a weakening line (38) within the pasting or welding zone.

* * * * *